US00PP16685P2

(12) United States Plant Patent
Koning

(10) Patent No.: US PP16,685 P2
(45) Date of Patent: Jun. 20, 2006

(54) LAVENDER PLANT NAMED 'ANOUK'

(50) Latin Name: *Lavandula stoechas*
Varietal Denomination: Anouk

(75) Inventor: Lammert Koning, Sappemeer (NL)

(73) Assignee: Koning Smit Holding N.V., Curaçao (NL)

( * ) Notice: Subject to any disclaimer, the term of this patent is extended or adjusted under 35 U.S.C. 154(b) by 61 days.

(21) Appl. No.: 11/113,371

(22) Filed: Apr. 23, 2005

(51) Int. Cl.
*A01H 5/00* (2006.01)

(52) U.S. Cl. ..... Plt./226
(58) Field of Classification Search ..... Plt./226
See application file for complete search history.

(56) References Cited

U.S. PATENT DOCUMENTS

PP15,208 P2 * 10/2004 McNaughton ..... Plt./226
PP15,571 P2 * 2/2005 Robb ..... Plt./226

OTHER PUBLICATIONS

UPOV ROM GTITM Computer Database, GTI Jouve Retrieval Software 2005/03 Citations for 'Anouk'.*

* cited by examiner

*Primary Examiner*—Kent L. Bell
*Assistant Examiner*—W. C. Haas
(74) *Attorney, Agent, or Firm*—C. A. Whealy

(57) ABSTRACT

A new and distinct cultivar of Lavender plant named 'Anouk', characterized by its compact, upright, somewhat outwardly spreading and mounded plant habit; freely branching habit; dense and bushy plant form; greyed green-colored foliage; and large purple violet-colored flowers with violet-colored terminal flower bracts.

2 Drawing Sheets

Botanical designation: *Lavandula stoechas.*
Cultivar denomination: 'Anouk'.

BACKGROUND OF THE INVENTION

The present Invention relates to a new and distinct cultivar of Lavender plant, botanically known as *Lavandula stoechas*, and hereinafter referred to by the name 'Anouk'.

The new Lavender is a product of a planned breeding program conducted by the Inventor in Sappemeer, The Netherlands. The objective of the breeding program was to create new Lavender cultivars with attractive flowers and good garden performance.

The new Lavender originated from a cross-pollination in May, 2000 of the *Lavandula stoechas* cultivar Fat Had, not patented, as the female, or seed, parent with the *Lavender stoechas* cultivar NA-17, not patented, as the male, or pollen, parent. The new Lavender was discovered and selected by the Inventor as a single flowering plant within the progeny of the stated cross-pollination grown in a controlled environment in Sappemeer, The Netherlands.

Asexual reproduction of the new cultivar by terminal cuttings at Sappemeer, The Netherlands, since 2002, has shown that the unique features of this new Lavender are stable and reproduced true to type in successive generations.

SUMMARY OF THE INVENTION

Plants of the cultivar Anouk have not been observed under all possible environmental conditions. The phenotype may vary somewhat with variations in environment such as temperature and light intensity without, however, any variance in genotype.

The following traits have been repeatedly observed and are determined to be the unique characteristics of 'Anouk'.

These characteristics in combination distinguish 'Anouk' as a new and distinct cultivar:

1. Compact, upright, somewhat outwardly spreading and mounded plant habit.
2. Freely branching habit, dense and bushy plant form.
3. Greyed green-colored foliage.
4. Large purple violet-colored flowers with violet-colored terminal flower bracts.

Plants of the new Lavender differ from plants of the female parent, the cultivar Fat Had, in the following characteristics:

1. Plants of the new Lavender and the cultivar Fat Had differ in leaf coloration.
2. Plants of the new Lavender have larger inflorescences with larger terminal flower bracts than plants of the cultivar Fat Had.

Plants of the new Lavender differ from plants of the male parent, the cultivar NA-17, in the following characteristics:

1. Plants of the new Lavender and the cultivar NA-17 differ in leaf coloration.
2. Plants of the new Lavender have fewer terminal flower bracts than plants of the cultivar
3. Plants of the new Lavender are more winter hardy than plants of the cultivar NA-17.

Plants of the new Lavender can be compared to plants of the Lavender cultivar Alexandra, not patented. In side-by-side comparisons conducted in Sappemeer, The Netherlands, plants of the new Lavender differed from plants of the cultivar Alexandra in the following characteristics:

1. Plants of the new Lavender were more compact and denser than plants of the cultivar Alexandra.
2. Plants of the new Lavender had larger inflorescences than plants of the cultivar Alexandra.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which more accurately describe the actual colors of the new Lavender.

The photograph on the first sheet comprises a side perspective view of a typical flowering plant of 'Anouk' grown in a container.

The photograph at the top of the second sheet comprises a close-up view of a typical inflorescence of 'Anouk'.

The photograph at the bottom of the second sheet comprises a close-up view of typical leaves of 'Anouk'.

DETAILED BOTANICAL DESCRIPTION

In the following description, color references are made to The Royal Horticultural Society Colour Chart, 2001 Edition, except where general terms of ordinary dictionary significance are used. Plants used for the aforementioned photographs and following description were grown under conditions which closely approximate commercial production conditions during the fall in an outdoor nursery in Boskoop, The Netherlands for about two years in 17-cm containers. During the production of the plants, day temperatures ranged from 4° C. to 20° C. and night temperatures ranged from 0° C. to 14° C.

Botanical classification: *Lavandula stoechas* cultivar Anouk.

Parentage:

*Female, or seed, parent.*—*Lavandula stoechas* cultivar Fat Had, not patented.

*Male, or pollen, parent.*—*Lavender stoechas* cultivar NA-17, not patented.

Propagation:

*Type cutting.*—Terminal vegetative cuttings.

*Time to initiate roots, summer and winter.*—About 10 days at 18° C.

*Time to produce a rooted young plant, summer.*—About 60 days at 20° C.

*Time to produce a rooted young plant, winter.*—About 70 days at 20° C.

*Root description.*—Fine, fibrous.

*Rooting habit.*—Freely branching; dense.

Plant description:

*Form.*—Perennial plant; compact, upright, somewhat outwardly spreading and mounded plant form. Freely basal branching habit with about 80 lateral branches per plant; dense and bushy plant habit. Flowers in verticillasters on crowded spikes with showy terminal flower bracts. Moderately vigorous. Plants aromatic.

*Plant height.*—About 36 cm.

*Plant width.*—About 31 cm.

*Lateral branch description.*—Length: About 19.7 cm. Diameter: About 2 mm. Internode length: About 1.6 cm. Strength: Strong. Aspect: Mostly upright to somewhat outward. Texture: Tomentose; wooly. Color, immature: 138B. Color, mature: 200D.

*Foliage description.*—Arrangement: Opposite, simple; sessile. Length: About 2.8 cm. Width: About 4 mm. Shape: Linear. Apex: Acute. Base: Cuneate. Margin: Entire; revolute. Texture, upper and lower surfaces: Tomentose; wooly. Venation pattern: Pinnate. Color: Developing foliage, upper surface: Between N138B and 189B. Developing foliage, lower surface: 138B. Fully expanded foliage, upper surface: 189A. Fully expanded foliage, lower surface: N138C. Venation, upper surface: 189A. Venation, lower surface: N138C.

Flower description:

*Flower arrangement and shape.*—Small single salverform flowers in compact verticillasters on crowded terminal spikes. Freely flowering, about 90 open flowers and flower buds per spike; flowers tubular with five lobes; inflorescences with showy terminal bracts.

*Natural flowering season.*—Continuous through the summer.

*Time to flowering.*—Early flowering, plants begin to flower about two months after planting.

*Flower longevity on the plant.*—About ten days. Flowers, not persistent; terminal flower bracts, persistent.

*Flower buds.*—Length: About 5 mm. Diameter: About 2 mm. Shape: Elliptic. Color: 138B to 144A to 144B; towards the base, 144C.

*Inflorescence size.*—Height: About 4.4 cm. Diameter: About 1.7 cm.

*Flowers.*—Diameter: About 3 mm. Depth (height): About 4 to 5 mm.

*Petals.*—Arrangement: Five, fused into a tube. Length: About 7 mm. Width: About 1.2 mm. Shape: Roughly spatulate. Apex: Rounded. Margin: Entire. Texture, upper and lower surfaces: Smooth, glabrous. Color: When opening, upper and lower surfaces: N87B to N87C; towards the base, 85C to 85D. Fully opened, upper and lower surfaces: 79B to 83A; towards the base, 85C to 85D; color becoming closer to 79A with development.

*Terminal flower bracts.*—Arrangement: About four in a single whorl at inflorescence apex. Length: About 1.6 cm. Width: About 7 mm. Shape: Obovate. Apex: Obtuse. Base: Cuneate. Margin: Entire; undulate. Texture, upper and lower surfaces: Smooth, glabrous. Color, immature, upper and lower surfaces: 83A to 83B. Color, mature, upper and lower surfaces: 83A to 83B; venation, N81A.

*Flower bracts.*—Arrangement: Each whorl of flowers subtended by a flower bract. Length: About 8 mm. Width: About 7 mm. Shape: Broadly rhomboidal. Apex: Broadly acute. Base: Cuneate. Margin: Entire. Texture, upper and lower surfaces: Tomentose; wooly. Color, upper and lower surfaces: 146C to 146D; venation, 146A to 147A.

*Sepals.*—Arrangement: Five sepals fused into a tube; campanulate. Length: About 5 mm. Width: About 1.5 mm. Apex: Acute. Base: Fused. Margin: Entire. Texture, upper and lower surfaces: Tomentose; wooly. Color, immature, upper and lower surfaces: 138B to 144A to 144B; towards the base, 144C. Color, mature, upper surface: 138B to 144A to 144B; towards the base, 144C. Color, mature, lower surface: 138B to 144A; towards the base, 144B.

*Peduncle.*—Strength: Strong. Length: About 3.7 cm. Diameter: About 2 mm. Aspect: Mostly upright. Color: 138B to 138C.

*Reproductive organs.*—Stamens: Quantity per flower: Four. Filament length: About 0.5 mm. Anther shape: Reniform. Anther length: About 0.5 mm. Anther color: N167A to N167B. Pollen amount: Scarce. Pollen color: N167A to N167B. Pistils: Quantity per flower: One. Pistil length: About 4 mm. Stigma shape: Club-shaped. Stigma color: 79A to 79B to 83A. Style length: About 3.6 mm. Style color: Whitish. Ovary color: 145D.

*Seed/fruit*.—Seed and fruit production has not been observed.

Disease/pest resistance: Plants of the new Lavender have not been noted to be resistant to pathogens and pests common to Lavender.

Weather tolerance: Plants of the new Lavender have exhibited good tolerance to rain and wind and have been observed to tolerate temperatures from −12° C. to 40° C.

It is claimed:

1. A new and distinct cultivar of Lavender plant named 'Anouk', as illustrated and described.

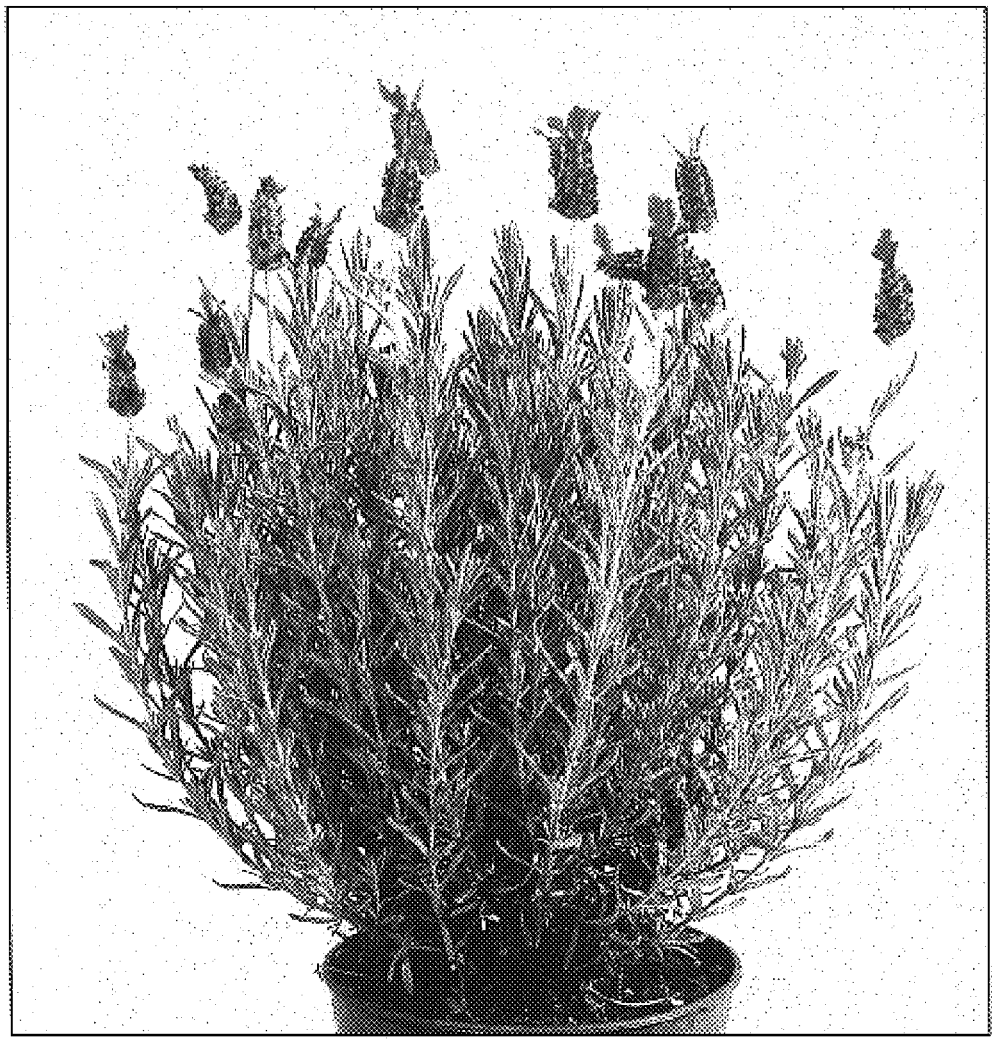

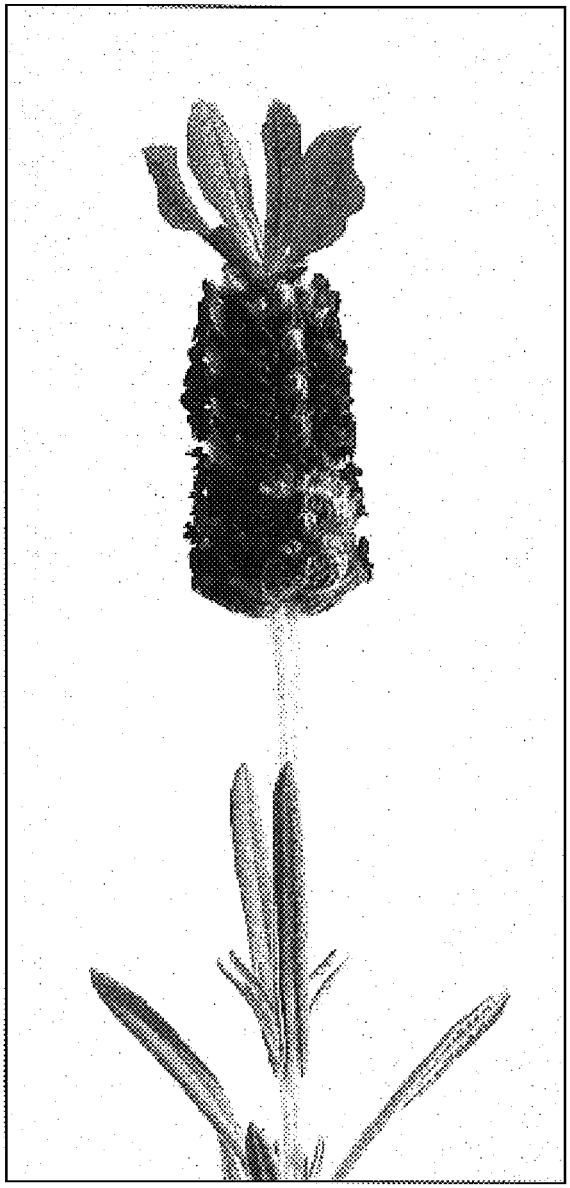
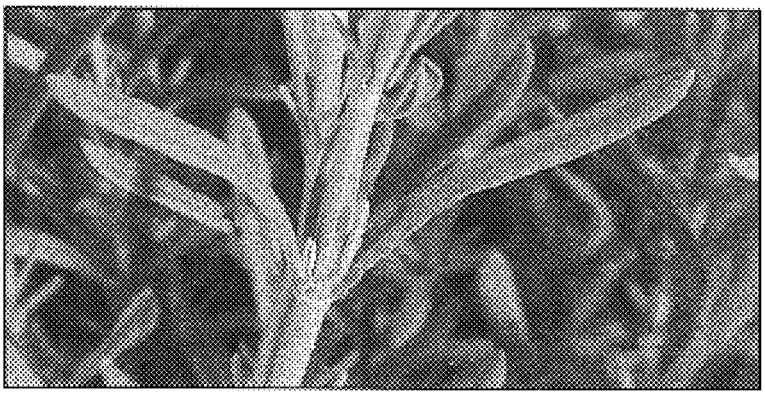

* * * * *